United States Patent [19]

Poleschinski et al.

[11] Patent Number: 4,969,037
[45] Date of Patent: Nov. 6, 1990

[54] ARRANGEMENT FOR ILLUMINATING AND DETECTING PARTS IN AN IMAGE PROCESSING SYSTEM

[75] Inventors: Richard Poleschinski; Detlef Gerhard, both of Munich, Fed. Rep. of Germany

[73] Assignee: Siemens Aktiengesellschaft, Berlin and Munich, Fed. Rep. of Germany

[21] Appl. No.: 387,754

[22] Filed: Aug. 2, 1989

[30] Foreign Application Priority Data

Aug. 11, 1988 [DE] Fed. Rep. of Germany ....... 3827302

[51] Int. Cl.$^5$ ............................................. H04N 7/18
[52] U.S. Cl. .................................... 358/106; 358/113; 250/223 B; 356/240
[58] Field of Search ............... 358/113, 225, 101, 106, 358/107; 250/223 B; 356/240, 428

[56] References Cited

U.S. PATENT DOCUMENTS

| | | | |
|---|---|---|---|
| 4,026,414 | 5/1977 | Ellinger | 250/223 B X |
| 4,293,219 | 10/1981 | Ducloux | 250/223 B X |
| 4,454,542 | 6/1984 | Miyorazawa | 358/106 |
| 4,775,889 | 10/1988 | Yoshida | 358/106 |

FOREIGN PATENT DOCUMENTS

| | | |
|---|---|---|
| 0047936 | 3/1982 | European Pat. Off. . |
| 0209077 | 1/1987 | European Pat. Off. . |
| 2916361 | 11/1980 | Fed. Rep. of Germany . |
| 2042164A | 9/1980 | United Kingdom . |
| 2159617A | 12/1985 | United Kingdom . |

OTHER PUBLICATIONS

Industrie–Elektrik and Electronic, vol. 29, 1984, No. 9, pp. 60-62.
Electronik 4/Feb. 19, 1988, pp. 121-126.

*Primary Examiner*—Victor R. Kostak
*Attorney, Agent, or Firm*—Hill, Van Santen, Steadman & Simpson

[57] ABSTRACT

An optical pick-up device for image processing systems has an objective for generating an optical image of a subject to be registered, an image-to-signal transducer, particularly a CCD camera that converts the optical image into a video signal and an illumination device for illumination of the subject to be registered in incident light. The rugged and high-performance illumination device, that yields an optimum light distribution in the plane of registration, has a plurality of infrared diodes that are arranged with equal spacing on at least one circle coaxial with the optical axis of the objective. It also has at least one annular deflection device that is similarly arranged coaxial with the optical axis. This deflection device concentrates the light emitted by the infrared diodes obliquely onto the subject from all sides.

26 Claims, 3 Drawing Sheets

ARRANGEMENT FOR ILLUMINATING AND DETECTING PARTS IN AN IMAGE PROCESSING SYSTEM

BACKGROUND OF THE INVENTION

1. Field of the Invention

The invention relates to an image processing system which may be utilized to recognize and measure parts, while using various illumination techniques for its optical pick-up stage.

2. Description of the Prior Art

Image processing systems that are referred to as BVS produce information about a given subject, then supply that information to a computer for processing. For best results, an image processing system should first obtain critical information about the image to be processed. For increased processing speed with simultaneous reduction of the outlay, it is advantageous to reduce the quantity of data as early as possible with respect to the desired information (see the periodical "industrie-elektrik+electronic", Vol. 29, 1984, No. 9, pages 60 through 62). To achieve this data reduction as early as pick-up of the image, it is known (from the periodical "Elektronik", 4/19 Feb. 1988, pages 121 through 126), to employ active infrared light sources that are arranged to irradiate the subject to be measured. To achieve an adequately high signal-to-noise spacing between the background radiation and the infrared source, diodes with pulsed power sources and emission in the infrared wavelength range are used.

Image processing systems are increasingly used for recognizing and measuring parts. The precise matching of the subject illumination to the objective is essential for maintaining accuracy. Common difficulties are, in particular, reflections, an inadequate subject illumination caused by different luminescent intensities over the surface, as well as the ruggedness and weight of the illumination means.

In conventional optical pick-up stages for image processing systems, normal incandescent lamps, halogen lamps, and fluorescent tubes are commonly used for the illumination of the subjects. The light of these illumination sources shines directly onto the subject or it is directed onto the subject by mirrors or beam splitters. Indirect illumination of the subject by diffused light is also well-known. The disadvantages of these illumination devices are their great sensitivity and the requirement that they be synchronized with the video signal of the image-to-signal transducer and the camera, since they operate on alternating currents. In these known illumination devices, a diaphragm controls the brightness.

SUMMARY OF THE INVENTION

An object of the invention is to provide a rugged and high-performance optical pick-up stage with an illumination source and deflector for an image processing system. In the present invention, the illumination source can be accurately matched to the subject.

This object is inventively achieved by having an image-to-signal transducer designed as a semiconductor camera. The present invention uses infrared emitting diodes to serve as the illumination means. An annular deflector is used to concentrate the infrared light on the subject. The deflector is arranged coaxially with the optical axis of the objective. The optical pick-up stage of the invention has diodes that emit in the near infrared range, i.e. in a wavelength range between 750 nm and 1000 nm. These diodes are especially effective because their wavelength range lies in the spectral range where an image-to-signal transducer designed as a semiconductor camera (particularly a CCD camera), is most sensitive. These diodes have an extremely long life and their emission intensities can easily be controlled by varying their current input. A uniform illumination of the surface of the subject can be enhanced by an overlap of the radiation from the individual diodes. This is accomplished by a circular arrangement of diodes equally spaced around the circumference of an annular disk. The optical axis of this arrangement is through the center of the objective. Using a greater number of diodes on two or more concentric circles yields a higher intensity infrared field. This high intensity radiation can successfully illuminate an extremely large area. The deflector is arranged coaxially with the optical axis of the subject. This deflector is composed of a ring or of a plurality of rings which enables an optimum matching of the light distribution to be realized. This deflector can be adapted to change the incident angle of radiation to conform to the conditions of the subject and the illumination of the subject's surfaces. The especially low sensitivity of the pick-up stage and the simple operation without the requirement of a synchronization with the video signal of the image-to-signal transducer are other advantages of the present invention.

In a preferred embodiment of the invention, the emission and intensity of the diodes can be controlled by the input current. Therefore, the electrical signals generated by the image-to-signal transducer can be utilized for the control of the emission intensity of the diodes in a simple way. This illumination control can compensate for disturbances such as modification of the luminescent behavior of the diodes caused by aging or temperature influence, fluctuations in ambient light, different reflection behavior of the subjects or changes in the contrast and the image brightness caused by fluctuating distances between the subject surface and the objective.

A significantly more sophisticated illumination control can compensate for subjects that are tilted by dividing the diodes into groups and controlling each group's emission intensity separately. This is particularly advantageous when the diodes are combined into separately controllable groups by quadrants. Even pronounced light fluctuations caused by tilting can be compensated by separately controlling the four quadrants of the image area. In a feedback arrangement, brightness sensors may be used to determine what diode emission and intensity should be used. These brightness sensors receive light reflected off of the surface of the subject.

For simplification of the structural outlay, the diodes are preferably secured on a diode carrier designed as an annular disk. As needed, a plurality of such diode carriers can be used in a concentric arrangement.

In a first, preferred embodiment of the invention, the deflector is formed by an annular lens. Such annular lenses enable the incident angle of radiation to be easily adapted to what is needed.

In a second preferred embodiment, the advantages recited above can also be achieved when the deflector is formed by an annular mirror. The annular mirror is preferably formed by a conical housing section of an outer housing, whereby an especially compact structure can be realized given a low structural outlay. When the outside surface of the housing of the objective is mirrored, the inwardly directed light can be deflected onto the annular mirror. As a result, an even greater part of the emitted light power can be utilized for the illumination of the subject.

According to another preferred embodiment of the invention, illumination of the subject to be registered is in the dark field. Compared to bright field illumination, dark field illumination has the particular advantage of a far greater protection against disturbances caused by surface tilts of the subjects.

Another advantage of the invention is that the space requirement will be reduced because the illumination source surrounds the objective. For the same reason, it is also advantageous to arrange the deflector at approximately the same height as the objective. The objective means for illuminating and means for deflecting of the present invention form an extremely compact structure providing an improved control of the overall optical pick-up means.

DETAILED DESCRIPTION OF THE DRAWINGS

Figure 1:
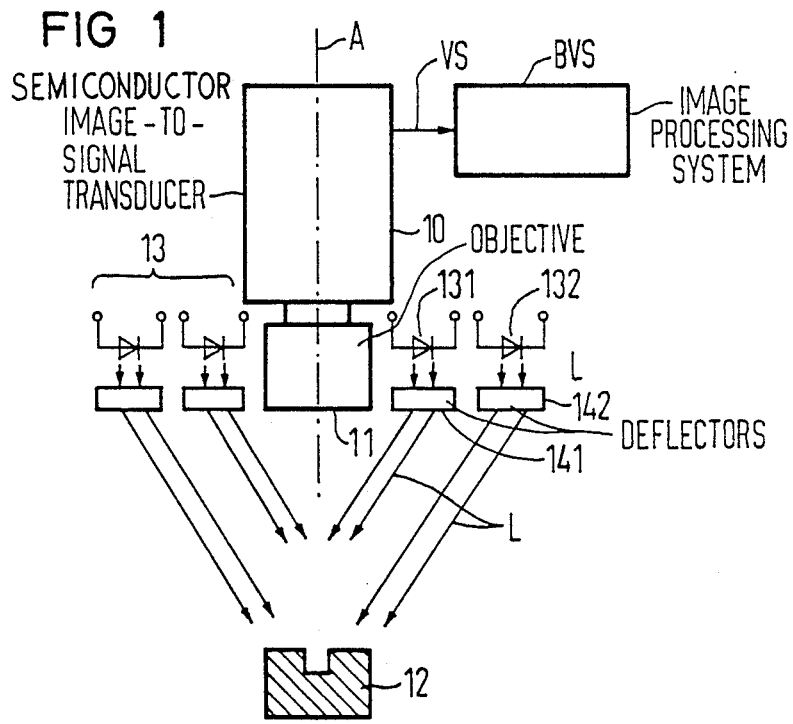
FIG. 1 is a cross-sectional view of an optical pickup stage for image processing systems according to the principles of the present invention.

FIG. 1 shows an optical pick-up stage for image processing systems. A semiconductor image-to-signal transducer 10 designed as a CCD has an underlying objective 11, whereby the image-to-signal transducer 10 and of the objective 11 have a common optical axis A. The objective 11 images a subject 12 onto the CCD sensor of the image-to-signal transducer 10 which converts this optical image into a chronological succession of electrical or video signals into a video signal VS. The video signal VS is fed into an image processing system BVS for further processing according to the particular job.

An illumination source 13 has a plurality of infrared emitting diodes such as diodes 131 and 132 for the illumination of the surface of the subject 12. As may be seen in FIG. 2, a total of 12 diodes 131 are equally spaced on an inner circle coaxial with the optical axis A and a total of 24 diodes 132 are equally spaced on an outer circle coaxial with the optical axis A. Both the inner coaxial circle and the outer coaxial circle are situated at the same height as the objective 11. The illumination means 13 is arranged so as to surround the objective 11. The light L emitted by the diodes 131 is obliquely concentrated onto the subject 12 from all sides via an annular, inner deflector 141 arranged coaxially with the optical axis A. Similarly, the light L emitted by the diodes 132 is obliquely concentrated onto the subject 12 from all sides via an annular, outer deflector 142 that is also arranged coaxially with the optical axis A. Both the inner deflector 141 and the outer deflector 142 are at the height of and surrounding the objective 11.

The deflectors 141 and 142 are designed for the illumination of the surface of the subject 12 in the dark field, whereby different incident angles of the radiation are also possible. In any case, the incident angle of the radiation is easily adapted to the conditions of the subject surface and to the job to be completed. As a result, a uniform illumination of the subject surface will occur.

Figure 2:
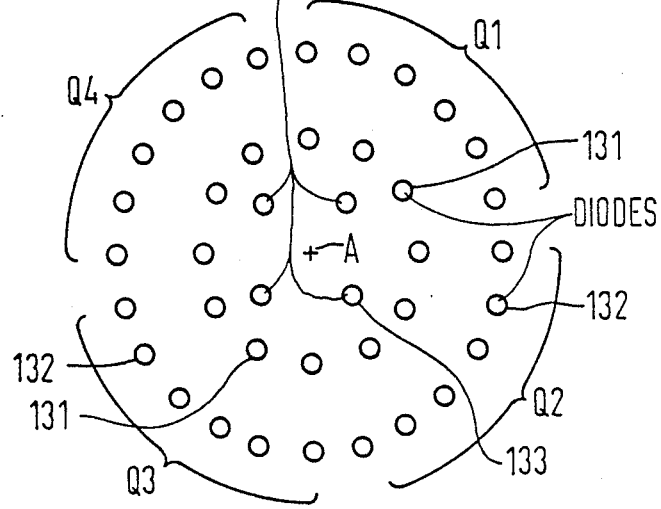
FIG. 2 is a plan view of the arrangement of diodes and brightness sensors in the pick-up stage of FIG. 1.

The emission intensity of the infrared emitting diodes 131 and 132 is dependent on the current passage through them. Therefore, the intensity can be controlled via the current in a simple way. This control of current can be separated into the inner and outer circle diode groups or can be separated into quadrants of diode groups. As shown in FIG. 2, the diodes 131 and 132 are combined into separately controllable quadrants Q1 through Q4, whereby a brightness sensor 133 is allocated to each of these quadrants. These brightness sensors 133 receive light L emitted by the diodes 131 and 132 and reflected light from the surface of the subject 12. A single brightness sensor only receives light from its assigned quadrant. Therefore, a control circuit (to be set forth in detail later) can be used to control the emission intensity of the diodes 131 and 132 in the allocated quadrant.

Figure 3:
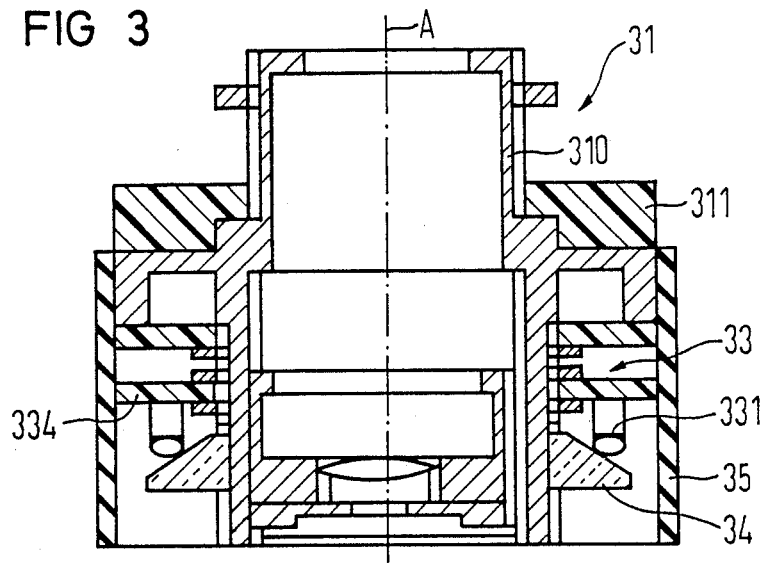
FIG. 3 is a cross-sectional view of a first embodiment of an objective having an illumination source integrated therewith.

FIG. 3 shows a longitudinal section through a first embodiment of the present invention of an objective with an integrated illumination system. An objective housing 310, a clamp cover 311, an achromatic objective 312 and a diaphragm 313 of the objective 31 whose optical axis is again referenced A, are shown in FIG. 3. The lower part of the objective housing 310 is surrounded by a sturdy, annular diode carrier 334 that is aligned coaxially relative to the optical axis A and on which, for example, sixteen infrared emitting diodes 331 are equally spaced over the circumference. The diodes 331 and the diode carrier 334 form an illumination system 33. A deflector 34 fashioned as an annular lens is attached onto the objective housing 310 directly below the illumination means 33. The deflector 34 is also aligned coaxially relative to the optical axis A. By use of this deflector, the light emitted by the diodes 331 will be obliquely concentrated onto the subject (not shown in detail in FIG. 3) from all sides. The deflection angle of the deflector 34 or the incident angle of the radiation is adjusted so that the illumination on the subject is at an optimum. A protective cap 35 is affixed onto an annular shoulder of the objective housing 310 and onto the diode carrier 334. This cap 35 protects the illumination system 33 and the deflector 34.

Figure 4:
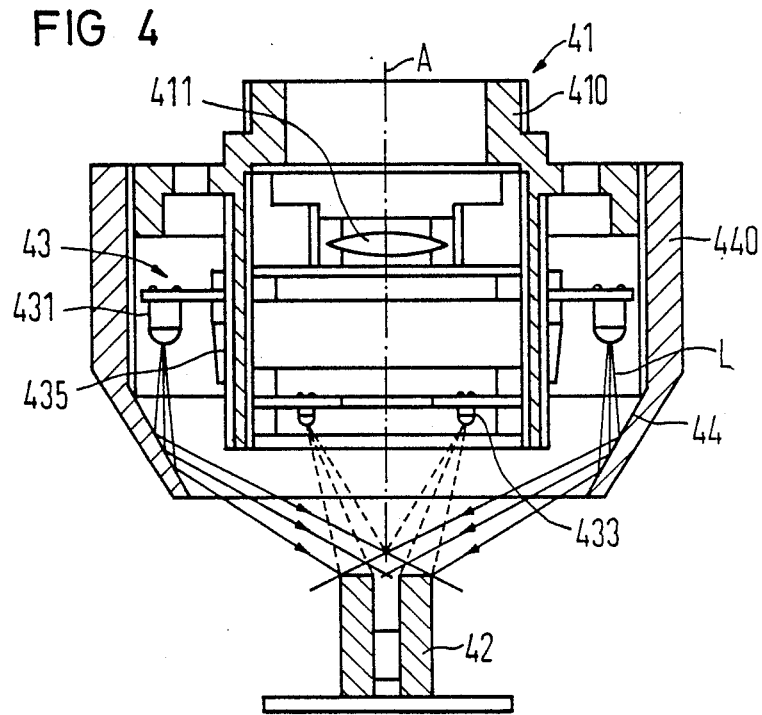
FIG. 4 is a cross-sectional view of a second embodiment of an objective and integrated illumination source.

FIG. 4 shows a longitudinal section through a second embodiment of the present invention of an objective having an integrated illumination system. The objective housing 410 and a lens 411 of the objective 41 whose optical axis is again referenced by A, are shown in FIG. 4. The lower part of the objective housing 410 is surrounded by a sturdy annular diode carrier 434 which is aligned coaxially relative to the optical axis A. By way of example, infrared emitting diodes 431 are arranged on this diode carrier 434 in equal spacing over the circumference. The diodes 431 and the diode carrier 434 form an illumination system 43. A deflection means 44 that is aligned coaxially relative to the optical axis A and is fashioned as an annular mirror is arranged under the illumination system 43. From all sides by the deflector 44, the light L emitted by the diodes 431 is obliquely concentrated onto the surface of a subject 42 which is arranged under the objective 41. The deflection angle of the deflector 44 or the incident angle of the radiation is matched so that the subject 42 will receive optimum illumination. The subject 42 is a coil whose core hole is to be recognized with the image processing system BVS (FIG. 1). A range of 50°-60° for the incident angle of the light L has proven advantageous for this job.

The aforementioned deflector 44 is a component part of an outer protective cap 440 that is affixed onto an annular shoulder of the objective housing 410. The lower conical region is mirrored on the inside for the formation of the annular lens. The outside surface of the objective housing 410 also has a mirrored surface 435. It is formed in the same region where the inside, conical mirroring is to achieve an even better light yield.

Brightness sensors 433 are arranged in the lower, inside region of the objective 41 and at the approximate height of the deflector 44. These brightness sensors 433 receive the light L emitted by the diodes 431 reflected from the surface of the subject 42. These sensors are used for control of the emission intensity of the diodes 431.

Figure 5:
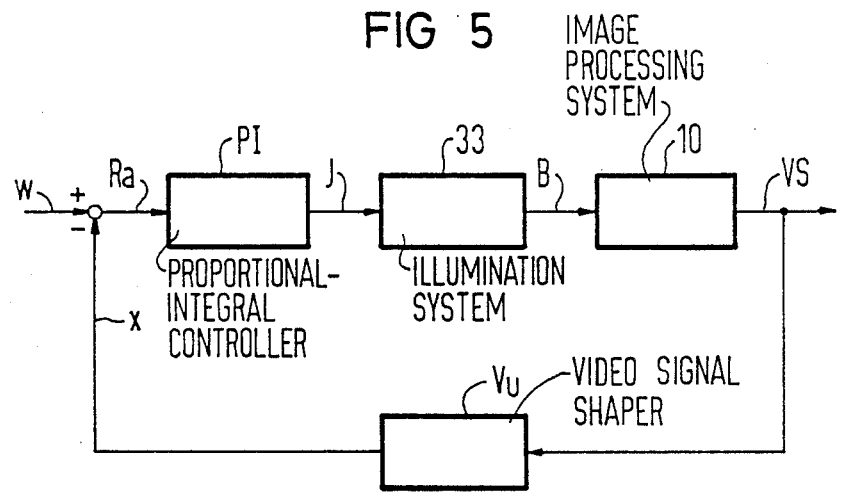
FIG. 5 is a schematic diagram of the block circuit diagram of the control circuit of FIG. 3.

FIG. 5 shows the block circuit diagram of the control circuit of an illumination control suitable for the embodiment of FIG. 3. A proportional-integral controller PI, the illumination system 33 (also see FIG. 3) and the image-to-signal transducer 10 (also see FIG. 1) are arranged in succession in this control circuit, whereby the arrow B represents the image of the respective subject. The video signal VS generated by the image-to-signal transducer 10 is supplied to a video signal shaping VU whose output signal, as regulating variable x, is compared to the rated value w of the luminesce intensity at the input of the controller PI for forming the repetitive error. Given deviation, the output quantity y of the controller PI changes, so that the luminescent intensity of the illumination system 33 can be set to the desired value via the current passage across the diodes. The particular subject will determine what value at W is appropriate to achieve optimum illumination.

Figure 6:
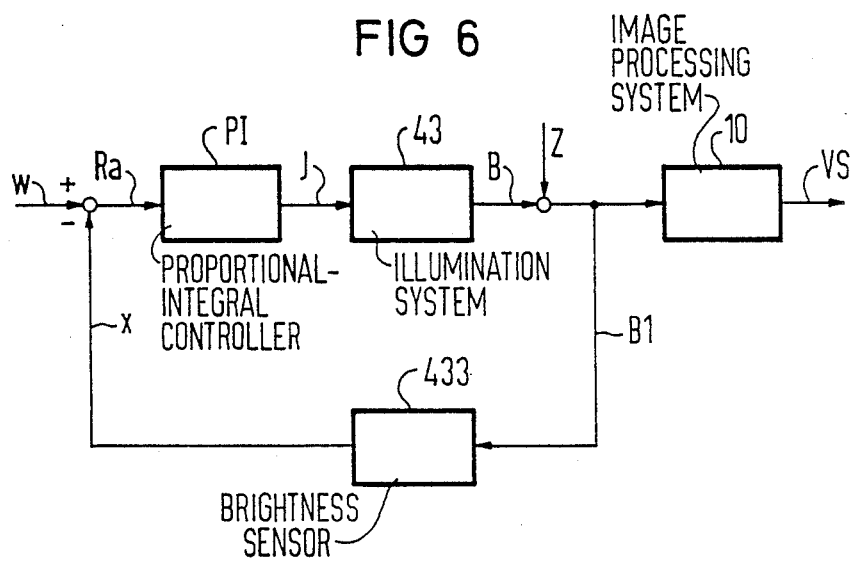
FIG. 6 is a schematic diagram of the block circuit diagram of the control circuit of FIG. 4.

FIG. 6 shows the block circuit diagram of the control circuit of an illumination control suitable for the embodiment of FIG. 4. In this modification, the influence of a disturbance Z acting on the image B is inputted between the illumination system 43 and the image-to-signal transducer 10. Since a quadrant-by-quadrant control of the luminescent intensity is provided here, the video signal VS is not suitable for an illumination feedback. Signal B, varied by the influence of the disturbance Z, is supplied to the brightness sensor 433 (see FIG. 4) as signal B1. The output quantity of this brightness sensor 433 is represented by regulating variable x. The formation of the repetitive error Ra, by comparing the regulating variable x to a rated value w prescribed here for the respective quadrant, corresponds to the embodiment of FIG. 5. Different surface illuminations, that have arisen due to tilting of the subject 42 (see FIG. 4), can be corrected with 4 of the quadrant controls illustrated in FIG. 6.

The infrared emitting diodes 131, 132, 331, and 431 that are recited in the above-described embodiments, are based on either gallium arsenide (GaAs) or gallium aluminum arsenide (GaAlAs). Semiconductor cameras such as CCD cameras, particularly Si semiconductor cameras, are especially well adapted to the emission spectrum of these infrared emitting diodes because of their sensitivity. In GaAs infrared emitting the emission wavelength is about 900 nm. In GaAlAs infrared emitting such as type SFH 480-2 of Siemens AG, the wavelength of the emitted radiation is between 750 and 1000 nm.

Although modifications and changes may be suggested by those skilled in the art, it is the intention of the inventors to embody within the patent warranted hereon all changes and modifications as reasonably and properly come within their contribution to the art.

We claim as our invention:

1. An optical pick-up for use in an image processing system, said pick-up means comprising:
    objective means for generating an optical image of a subject, said objective means having an optical axis;
    semiconductor means for converting said optical image into electrical signals;
    illumination means for illuminating said subject, said illumination means having a plurality of infrared diodes emitting infrared radiation, each of said diodes having an emission intensity, said diodes laterally surrounding said objective means, said plurality of infrared diodes equally spaced around at least one circle, said at least one circle being in coaxial alignment with said optical axis;
    annular deflection means for deflecting said infrared radiation emitted from said diodes,
    said annular deflection means obliquely concentrating said infrared radiation emitted from said diodes onto said subject from all sides,
    means for housing said optical pick-up means, said means for housing having an objective housing and an outer housing.

2. An optical pick-up as in claim 1, wherein said illumination means is in a dark field.

3. An optical pick-up as in claim 1, wherein said emission intensity of said diodes is current dependent.

4. An optical pick-up as in claim 1, wherein said electrical signals are used as regulating variables for controlling said emission intensity of the diodes.

5. An optical pick-up as in claim 4, wherein a first electrical signal regulates said control of emission intensity for a first group of diodes and a second electrical signal regulates said control of emission intensity for a second group of diodes.

6. An optical pick-up as in claim 5, wherein said diodes are divided into at least 4 groups.

7. An optical pick-up as in claim 5, wherein the control of emission intensity of each of said groups of diodes is regulated by a separate brightness sensor.

8. An optical pick-up as in claim 1, wherein said diodes are secured on an annular disk to form a diode carrier.

9. An optical pick-up as in claim 1, wherein said annular deflection means is arranged at the same height as said objective means.

10. An optical pick-up as in claim 1, wherein an outside surface of said objective housing carries a mirror coating.

11. An optical pick-up as in claim 1, wherein said objective means, said illumination means and said annular deflection means form an integrated structure.

12. An optical pick-up as in claim 1, wherein said annular deflection means comprises an annular mirror.

13. An optical pick-up as in claim 1, wherein said annular deflection means comprises an annular lens.

14. An optical pick-up for use in an image processing system, said pick-up comprising:

objective means for generating an optical image of a subject, said objective means having an optical axis;

semiconductor image-to-signal converting means for converting said optical image into electrical signals;

illumination means for illuminating said subject, said illumination means having a plurality of infrared diodes equally spaced in a circle, said circle being coaxial with said optical axis, said diodes emitting infrared radiation at an emission intensity; and, annular deflection means for obliquely concentrating said infrared radiation from said diodes onto said subject.

15. An optical pick-up as recited in claim 14, wherein said emission intensity is controlled by varying a flow of current through said diodes.

16. An optical pick-up as recited in claim 15, wherein said electrical signals of said semiconductor image-to-signal converting means are utilized as regulating variable to control said flow of current through said diodes.

17. An optical pick-up as recited in claim 14, wherein said diodes are grouped in a plurality of groups, each group of said plurality of groups having its respective emission intensity controllable by varying a flow of current therethrough.

18. An optical pick-up as recited in claim 17, wherein each of said plurality of groups is formed by combining groups of said diodes according to quadrants.

19. An optical pick-up as recited in claim 17, further comprising brightness sensors for detecting light reflected from said subject and controlling said flow of current based on said reflected light.

20. An optical pick-up as recited in claim 14, further comprising an annular disk diode carrier having said diodes secured thereto.

21. An optical pick-up as recited in claim 14, wherein said annular deflection means comprises an annular lens.

22. An optical pick-up as recited in claim 14, wherein said annular deflection means comprises an annular mirror.

23. An optical pick-up as recited in claim 14, wherein said annular mirror is formed by a conical housing section of an outer housing, said outer housing having a mirrored surface.

24. An optical pick-up as recited in claim 14, wherein said plurality of said infrared diodes equally spaced in said circle surround said objective.

25. An optical pick-up as recited in claim 14, wherein said annular deflection means and said objective are located at approximately similar heights.

26. An optical pick-up as recited in claim 14, wherein said objective means, said illumination means, and said annular deflection means are integrated within a single housing.

* * * * *